(12) United States Patent
Yang

(10) Patent No.: US 7,341,834 B2
(45) Date of Patent: Mar. 11, 2008

(54) MULTIPLEXED ELECTROCHEMICAL DETECTION SYSTEM AND METHOD

(75) Inventor: Xing Yang, San Diego, CA (US)

(73) Assignee: Geneohn Sciences, Inc., San Diego, CA (US)

( * ) Notice: Subject to any disclaimer, the term of this patent is extended or adjusted under 35 U.S.C. 154(b) by 0 days.

(21) Appl. No.: 11/011,490

(22) Filed: Dec. 13, 2004

(65) Prior Publication Data
US 2005/0196776 A1 Sep. 8, 2005

Related U.S. Application Data

(60) Provisional application No. 60/529,800, filed on Dec. 15, 2003.

(51) Int. Cl.
*C12Q 1/68* (2006.01)
*C12M 1/36* (2006.01)
*G01N 15/06* (2006.01)

(52) U.S. Cl. ............ 435/6; 435/283.1; 435/288.4; 422/68.1; 422/82.01

(58) Field of Classification Search ............ None
See application file for complete search history.

(56) References Cited

U.S. PATENT DOCUMENTS

| | | | |
|---|---|---|---|
| 5,545,531 A * | 8/1996 | Rava et al. | ............ 435/6 |
| 6,331,441 B1 | 12/2001 | Balch et al. | |
| 6,468,742 B2 | 10/2002 | Nerenberg et al. | |
| 6,673,533 B1 * | 1/2004 | Wohlstadter et al. | ............ 435/6 |
| 2002/0090649 A1 * | 7/2002 | Chan et al. | ............ 435/7.1 |
| 2002/0123048 A1 * | 9/2002 | Gau, Jr. | ............ 435/6 |
| 2004/0022677 A1 * | 2/2004 | Wohlstadter et al. | ............ 422/52 |
| 2004/0086892 A1 | 5/2004 | Crothers et al. | |
| 2004/0086894 A1 | 5/2004 | Crothers et al. | |

FOREIGN PATENT DOCUMENTS

WO   WO 01/83674   11/2001

OTHER PUBLICATIONS

Steel et al., *Electrochemical Quantitation Of DNA Immobilized On Gold*, Analytical Chemistry, vol. 70, No. 22, pp. 4670-4677, Nov. 15, 1998.

(Continued)

*Primary Examiner*—BJ Forman
(74) *Attorney, Agent, or Firm*—Knobbe Martens Olson & Bear, LLP

(57) ABSTRACT

Multiplexed analysis of molecular structures of samples. A plurality of sample wells is arranged on a substrate. A plurality of electrodes is fabricated on a first side of the substrate. The electrodes are disposed on the side of the substrate exposed to the sample wells. The electrodes include working electrodes, counter electrodes, and optionally include reference electrodes. At least two of the sample wells includes a plurality of working electrodes. The plurality of electrodes is configured to allow electrochemical analysis of the associated sample wells in a multiplexed fashion. The plurality of electrodes is electrically coupled to an interface to a sample analysis system. The interface to the sample analysis system can include contacts or connections. The sample analysis system controls a signal to the electrodes in a multiplexed fashion and performs the electrochemical analysis.

19 Claims, 7 Drawing Sheets

OTHER PUBLICATIONS

Popovich et al., *New Strategies for Electrochemical Nucleic Acid Detection*, The Electrochemical Society Interface, Winter, 2002.

Vernon et al., *Bioelectric DNA Detection of Human Papillomaviruses Using eSensor™: A Model System for Detection of Multiple Pathogens*, BMC Infectious Diseases 2003, 3:12 available at http://www.biomedcentral.com/1471-2334/3/12.

Popovich, *Mediated Electrochemical Detection of Nucleic Acids for Drug Discovery and Clinical Diagnostics*, Originally published IVD Technology Apr. 2001, http://www.devicelink.com/grabber.php3?URL=http://www.devicelink.com/ivdt/archive/01/04/001/html (Oct. 20, 2003).

Brochure: Gamry Instruments, *PHE200 Physical Electrochemistry Software* http://www.gamry.com/Products/PHE200.htm (Oct. 17, 2003).

*Chronoamperometry/Chronocoulometry*, http://www.epsilon-web.net/Ec/manual/Techniques/ChronoI/ca.html (Oct. 17, 2003).

CHM 320—April Lectures Chapter 14, pp. 33-50 http://www.nau.edu/chem/faculty/ingram/images/CHM_320_April_Lectures.pdf.

\* cited by examiner

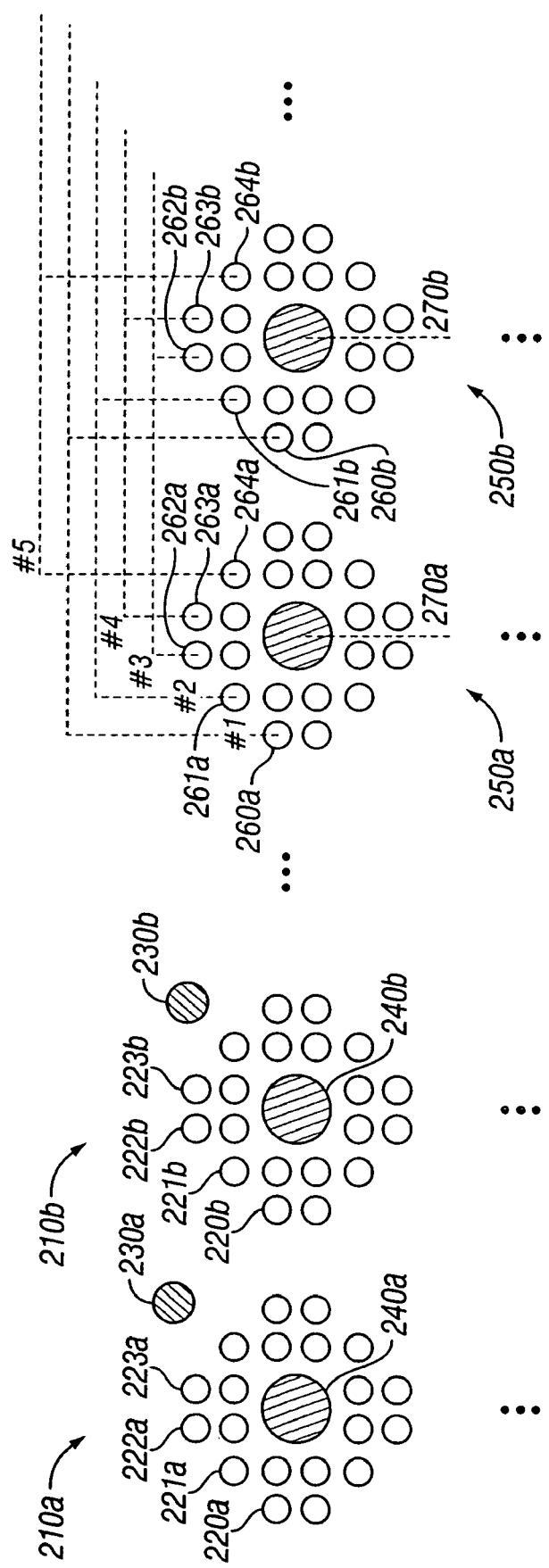

US 7,341,834 B2

MULTIPLEXED ELECTROCHEMICAL DETECTION SYSTEM AND METHOD

RELATED APPLICATIONS

This application claims the benefit of Provisional Application Ser. No. 60/529,800, filed Dec. 15, 2003, the disclosure of which is incorporated by reference herein in its entirety.

BACKGROUND OF THE INVENTION

1. Field of the Invention

The invention relates to electrochemical detection. More particularly, the invention relates to systems and methods of multiplexed electrochemical detection of samples using sample analysis containers and associated instrumentation.

2. Description of the Related Art

Molecular biology utilizes a wide variety of techniques to detect and identify the molecular structure of a sample. In particular, sequence analysis of DNA or RNA samples is performed to detect gene sequences, detect mutations in gene sequences, or detect gene expression levels of genes. Such sequence analysis is useful for diagnostic purposes as well as to facilitate genetic research and pharmaceutical development.

Sequence analysis can be performed by hybridizing a sample to polymer probes having known sequences. One method to detect nucleic acid hybridization is to detect a quantity of counterions surrounding the nucleic acid. Accordingly, hybridized nucleic acid tends to be surrounded by more of the counterions than would single stranded nucleic acid. The counterions are typically detected by an electrochemical reaction, for example by reduction of a trivalent ion to divalent; in this way, the counterions function as an electron transfer species.

Electrochemical quantitation is described in A. B. Steel et al., *Electrochemical Quantitation of DNA Immobilized on Gold*, Anal. Chem. 70:4670-77 (1998), hereby expressly incorporated by reference in its entirety. In this publication, Steel et al. describe the use of cobalt (III) trisbipyridyl and ruthenium (III) hexaamine as species which interact with surface-immobilized DNA.

The continuing development of sequence analysis as a tool for diagnostic purposes as well as genetic research and pharmaceutical development necessitates improvements in sequence analysis systems. The sequence analysis systems need to be flexible to allow testing of different batch sizes, reliable to allow repeatable test results, and low cost in order to facilitate the use in such diagnostic procedures such as patient sample screening.

SUMMARY OF THE INVENTION

Multiplexed electrochemical sample detection systems and methods are disclosed. The sample system allows for low cost, reliable, detection of polymer hybridization by electrochemically detecting hybridization of probes in sample wells. The system can be configured to detect one or more probe hybridizations within each sample well.

In one aspect, a plurality of sample wells is disposed on a substrate. Each of at least two sample wells includes a plurality of electrodes positioned on the substrate within the sample well. The plurality of electrodes includes a counter electrode and multiple working electrodes. At least one working electrode in a first sample well is electrically connected with a corresponding working electrode in a second sample well. In other embodiments, a reference electrode is included in each sample well. Polymer probes are attached to one or more working electrodes in a sample well. Hybridization of samples to the polymer probes can be detected using electrochemical processes. The electrochemical processes can include coulometry, voltammetry, amperometry, and the like.

BRIEF DESCRIPTION OF THE DRAWINGS

The features, objectives, and advantages of the invention will become apparent from the detailed description set forth below when taken in conjunction with the drawings, wherein like parts are identified with like reference numerals throughout.

FIGS. 2A-2D are functional diagrams of electrode configurations.

DETAILED DESCRIPTION OF THE PREFERRED EMBODIMENT

Figure 1B:
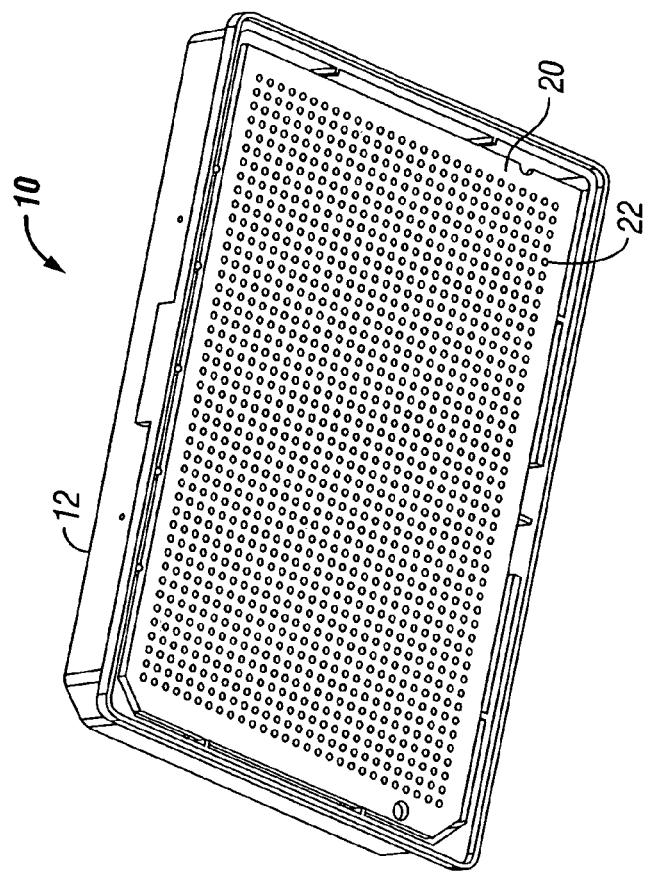
FIGS. 1A-1B are views of a sample well array.

Systems and methods for detecting polynucleotide hybridization using electrochemical quantitation are disclosed. An array of sample wells can be arranged on a substrate. The substrate can include electrodes positioned within each of the sample wells. The electrodes within each sample well can include working electrodes, a reference electrode, and a counter electrode. Probes, such as polymer probes can be attached to each of the working electrodes. The polymer probes attached to the various working electrodes can have the same or different base sequences.

Samples, which may contain target polymers, can be introduced to the sample wells. The target polymers can hybridize with complementary polymer probes that are attached to the various working electrodes.

Sample analysis instrumentation can selectively address the electrodes on the substrate to electrochemically detect polynucleotide hybridization of the target sample to the addressed electrode. In one embodiment, at least one working electrode positioned in each of the sample wells is electrically coupled to a corresponding working electrode in another sample well. Each sample well includes an independently addressable counter electrode. The sample analysis instrumentation can selectively address the electrodes associated with a particular sample well by applying a potential to the desired working electrode and counter electrode of the sample well. Alternatively, sample analysis instrumentation can simultaneously apply an electrical potential to multiple electrodes and a counter electrode within a selected sample well. Detection of polynucleotide hybridization can then be determined electrochemically, such as through coulometry or voltammetry.

Various techniques for isolating oligonucleotides and conducting hybridization assays are described in copending U.S. Pat. Application Ser. No. 60/424,656, filed Nov. 6, 2002; U.S. patent application Ser. No. 10/424,542 entitled "UNIVERSAL TAG ASSAY," filed Apr. 24, 2003; U.S. patent application Ser. No. 10/429,291 entitled "ELECTRO- CHEMICAL METHOD TO MEASURE DNA ATTACHMENT TO AN ELECTRODE SURFACE IN THE PRESENCE OF MOLECULAR OXYGEN," FILED May 2, 2003; all of which are hereby incorporated by reference in their entirety.

Embodiments of the invention include the detection of polynucleotide hybridization in a sample well or detection zone. Particular embodiments feature the use of a ruthenium complex in conducting an electrochemical assay. Electrochemical quantitation is described in A. B. Steel et al., *Electrochemical Quantitation of DNA Immobilized on Gold*, Anal. Chem. 70:4670-77 (1998), hereby expressly incorporated by reference in its entirety. An electrochemical assay that detects nucleic acid hybridization can use the general technique of Steele et al. Steel et al. describe the use of cobalt (III) trisbipyridyl and ruthenium (III) hexaamine as species which interact with surface-immobilized DNA.

Typically, in carrying out this technique, a plurality of nucleic acid probes, which are complementary to a sequence of interest, are used. In certain embodiments, probes range in length from about 10 to 25 base pairs, although probes having lengths shorter than 10 base pairs or longer than 25 base pairs may also be used. A length of about 17 base pairs can be advantageous in certain embodiments. The probe strands are positioned within a detection zone. In particular embodiments, the detection zone includes a surface, such as an electrode, in contact with a liquid medium, wherein the probe strands are immobilized on the surface such they are also in contact with the liquid medium. The surface can be a gold or carbon electrode that is coated with a protein layer such as avidin or streptavidin to facilitate the attachment of the nucleic acid probe strands to the electrode. The surface may also be a material other than gold or carbon. The protein layer may be porous, such that it allows ions to pass from the liquid medium to the electrode and vice versa. Attaching a probe strand to an avidin layer can include first binding the probe strand covalently to a biotin complex and then allowing the biotin to attach to the avidin. Alternatively, probe strands can be attached directly to the surface, for example, by using a thiol linkage to covalently bind nucleic acid to a gold electrode. As noted previously, carbon electrodes or electrodes of any other suitable conductor can also be used.

A target strand (a nucleic acid sample to be interrogated relative to the probe) can be contacted with the probe in any suitable manner known to those skilled in the art. For example, a plurality of target strands can be introduced to the liquid medium described above and allowed to intermingle with the immobilized probes. The number of target strands can exceed the number of probe strands in order to maximize the opportunity of each probe strand to interact with target strands and participate in hybridization. If a target strand is complementary to a probe strand, hybridization can take place. The stringency of hybridization can be adjusted. Techniques for detecting hybridization can include electrochemical analysis. The apparatus and methods used in the electrochemical detection system are described in further detail below in association with the figures.

Figure 1A:
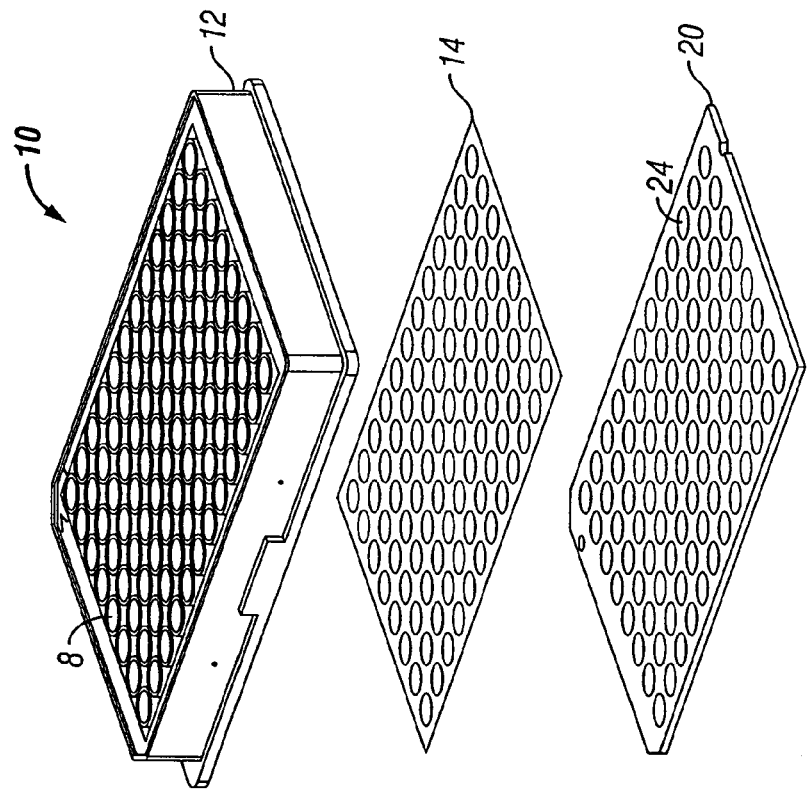

FIG. 1A is an exploded view of an embodiment of a sample array 10. The sample well 10 includes a well plate 12 having open, or bottomless, wells, for example 8. The plurality of open bottomed wells 8 can be arranged as an array in a multi-well plate. The well plate 12, alternatively referred to as a top plate or multi-well plate, can be attached to a substrate 20 using an adhesive layer 14. Thus, when assembled, the sample array 10 includes the well plate 12 with a bottom formed by the substrate 20. The substrate 20 can be, for example, a fiberglass substrate such as FR-4 printed circuit board material, glass, plastic, polymer, alumina, teflon, or some other suitable substrate material. The well plate 12 can be bonded to the substrate 20 using, for example, a UV or thermal cured adhesive 14 or a pressure sensitive adhesive 14. The adhesive layer 14 may be an adhesive sheet layer or may be a liquid layer that is deposited on the sample array 10 or the substrate 20. The well plate 12 need not be bonded to the substrate 20 using an adhesive layer 14, but may be bonded using any suitable technique, including ultrasonic welding, RF welding, laser welding, and co-extrusion or co-molding. Thus, where the sample array 10 is directly bonded to the substrate 20, the adhesive layer 14 may be omitted.

It will be appreciated that other techniques for attaching the substrate 20 to the well plate 12 may also be used, including co-molding of the two pieces together, RF welding, and providing a compression fit between the two; i.e., a mechanical attachment that physically presses the two pieces together so that there are no leaks. In this embodiment, for example, clamps or a snap fit can be used to provide the compression, and a gasket material can be provided on or between the well plate 12 and the substrate 20, if desired, to prevent leakage of liquid from wells of the well plate 12.

Thus, in one embodiment, the present invention includes a kit comprising the well plate 12 and the substrate 20, in a form in which the end user can assemble them together. This is advantageous, for example, if the user wants to attach polymer probe to the substrate 20 prior to assembly of the substrate to the well plate 12.

The substrate 20 includes one or more zones 24 that align or match up to the bottomless wells 8 of the well plate 12. One or more of the zones 24 can include a plurality of electrodes arranged on a first surface of the substrate 20. The electrodes are accessible through the well plate 12. A plurality of electrodes can be positioned in at least two of the sample wells in zones 24 on the substrate 20. It may be advantageous in some embodiments to position a plurality of electrodes in each of the sample wells or substantially all of the sample wells. Thus, a plurality of zones 24 can align with a plurality of sample wells 8. The following description describes the embodiment in which each of the sample wells includes the same number of electrodes. The plurality of electrodes within each of the sample wells includes a plurality of working electrodes, at least one counter electrode, and optionally can include at least one reference electrode.

The electrodes are typically electrically conductive and can be gold, carbon, platinum, palladium, or some other electrically conductive electrodes. Some or all of the electrodes can be fabricated with the same materials using the same processes. Alternatively, the electrodes can be fabricated of different materials or fabricated using different processes. One suitable method for the fabrication of carbon electrodes is described in further detail in U.S. Provisional Patent Application Ser. No. 60/530,065, entitled "CARBON ELECTRODE SURFACE FOR COVALENT ATTACHMENT OF DNA AND PROTEIN MOLECULES," filed concurrently herewith, hereby incorporated by reference in its entirety.

In one embodiment, carbon electrodes are fabricated on the side of the substrate 20 that is bonded to the well plate 12. The electrodes are coupled to a connector interface that can be disposed on the opposite side of the substrate 20 from the well plate 12, or alternatively at an edge or other suitable location. The connector interface can include one or more connectors or may include contact pads. It will be appreciated that any of the well-known techniques or configurations for connecting electrical circuits can be used. The number of contact pads or connections at the connector interface varies depending on the multiplexing scheme chosen for the electrodes. The number of contact pads can be less than, greater than, or equal to the number of electrodes disposed on the substrate 20. Advantageously, the multiplexing scheme reduces the number of contact pads to reduce the number of electrical connections that are made with associated analysis instruments. Different electrode configurations and multiplexing schemes are discussed in greater detail below.

The sample array 10 is shown configured with the dimensions of a standard 96 well plate. However, the sample array 10 need not be a 96 well plate, but can be an array of sample wells in a standard plate configuration, or a non-standard, custom array configuration. For example, the well plate 12 can include 16 wells, 24 wells, 48 wells, 96 wells, 384 wells, 1536 wells, or some other number of wells. Additionally, the sample array 10 is shown having wells configured to receive the samples and capture probes attached to the electrodes. However, the sample array 10 need not use sample wells, but may incorporate some other configuration for receiving the samples. The sample array 10 can use, for example, wells, dots, gels, cavities, channels, drops, and the like, or some other means for receiving a sample.

FIG. 1B is a bottom view of the sample array 10. In FIG. 1B the substrate 20 is bonded to the bottom of the well plate 12. The connector interface having contact pads, for example 22, can be seen on the exposed face of the substrate 12. The contact pads, for example 22, in the connector interface can be aggregated in a portion of the substrate 20 or may be distributed across the bottom surface of the substrate 20.

FIG. 2A is a functional diagram of an electrode configuration embodiment. The electrode configuration can be implemented in the substrate 20 of FIGS. 1A-1B. A first set of electrodes 210a can be positioned in a zone, for example 8, on the substrate 20 within a first sample well. Similarly, a second set of electrodes 210b can be positioned on the substrate within a second zone aligned with a second sample well. Additional sets of electrodes (not shown) can be positioned on the substrate such that they fall within other sample wells. In one embodiment, some or all of the electrodes in the first electrode set 210a are carbon electrodes. Similarly, some or all of the electrodes in the second electrode set 210b and additional electrode sets can be carbon electrodes. Alternatively, some or all electrodes in one or more of the electrode sets can be gold or some other material.

The first electrode set 210a in the illustrated embodiment includes twenty working electrodes, including those labeled 220a-223a, a reference electrode 230a, and a counter electrode 240a. The counter electrode 240a may be positioned to be substantially in the center of the twenty working electrodes, for example 220a-223a. The number of working electrodes need not be twenty and may be any number that can be physically positioned within a corresponding sample well. Additionally, as will be discussed in further detail below, the counter electrode 240a need not be positioned in the center of the working electrodes, for example 220a-223a.

The second electrode set 210b is configured similar to the first electrode set 210a. The second electrode set 210b also includes twenty working electrodes, for example 220b-223b, a reference electrode 230b, and a counter electrode 240b. Again, although not a requirement, the counter electrode 240b may be positioned to be substantially in the center of the twenty working electrodes, for example 220b-223b.

One or more polymer probes can be attached to each of the working electrodes, for example 220a. The polymer probes can be, for example, a nucleic acid such as RNA or DNA, a peptide, polypeptide, receptor, ligand, antibody, enzyme, and the like. A polymer probe may be directly attached to the electrode or may be attached to the electrode through an intermediate layer or intermediate structure using conventional techniques. A sample, which may include a target polymer, can be introduced to the sample well. Target polymers can hybridize with complementary polymer probes. Hybridization can be detected using electrochemical processes, such as coulometry or voltammetry, in accordance with any desired electrochemical detection scheme.

In one embodiment, a mutant probe can be attached to a first working electrode and a wild type probe attached to a different working electrode in the same electrode set. In this manner, an electrode set configuration having twenty working electrodes can be used to detect up to ten different mutations. Alternatively, some of the working electrodes can be used as controls, thus reducing the number of mutations that can be detected within an electrode set.

When the electrode configuration of FIG. 2A is repeated for each well in a 96 well plate, the number of electrodes fabricated on the substrate is very large. For example, there are 2112 electrodes disposed on the substrate of a 96 well plate with 20 working electrodes, a single counter electrode, and a single reference electrode in each well. This large number of electrodes poses a potential problem if each electrode is coupled to an independent contact on the connector interface of the substrate.

To reduce the number of connections that need to be made to an analysis instrument, the reference electrodes can be eliminated from the electrode sets in some embodiments. A three-electrode (reference, counter, and working electrodes) electrochemical configuration is commonly used to minimize the potential shift on the working electrode. However, if the current density through the working electrode is small enough, the potential shift can be fairly small with two-electrode configuration so as to be negligible. The elimination of reference electrodes from the substrate only eliminates one electrode for each sample well.

The working electrodes can be multiplexed to further reduce the number of connections at the connector interface of the substrate. FIG. 2B is a functional diagram of a multiplexing configuration. The multiplexing configuration is shown with only two electrode sets. However, the multiplexing configuration can be extended to more than two electrode sets.

A first electrode set 250a can be positioned on the substrate within a first sample well. Similarly, a second electrode set 250b can be positioned on the substrate within a second sample well.

The first electrode set includes twenty working electrodes, for example 260a-264a, and a counter electrode 270a. Similarly, the second electrode set 250b includes twenty working electrodes, for example 260b-264b, and a counter electrode 270b.

One embodiment of a multiplexing scheme reduces the number of connections at the connector interface by coupling together electrodes from multiple electrode sets. Instead of connecting electrodes to contact pads individually, corresponding working electrodes in each well are connected together. In other words, all #1 electrodes in every well are connected to a first contact pad on the backside of the substrate. All #2 electrodes in every well are similarly connected to a second contact pad on the backside of the substrate, and so on. All of the counter electrodes are connected individually to contact pads on the backside of the substrate. By using this multiplexing scheme, the total number of electrical connections in the previous example is reduced to 116.

In FIG. 2B, the first working electrode 260a of the first electrode set 250a is coupled to the first working electrode 260b of the second electrode set 250b.

Each sample well in the sample array can be read independently when performing electrochemical analysis of the sample wells in the plate. To analyze a particular sample well, an electrical potential is applied to a working electrode and to a corresponding counter electrode. Applying a potential to a working electrode simultaneously applies the potential to all working electrodes in other sample wells that are in common with the working electrode. However, the electrical potential can be individually controlled to the counter electrode in the desired sample well. Even though there is electrical potential on working electrodes of multiple wells, current only flows in the well whose counter electrode has the applied potential. All of the electrodes in all of the sample wells can be independently analyzed by selectively applying an electrical potential to a working electrode and the corresponding counter electrode. In this manner, for example, 20 different analyses using different probes attached to each working electrode can be performed in each well, giving 1920 analyses in a 96-well plate.

Figure 2D:
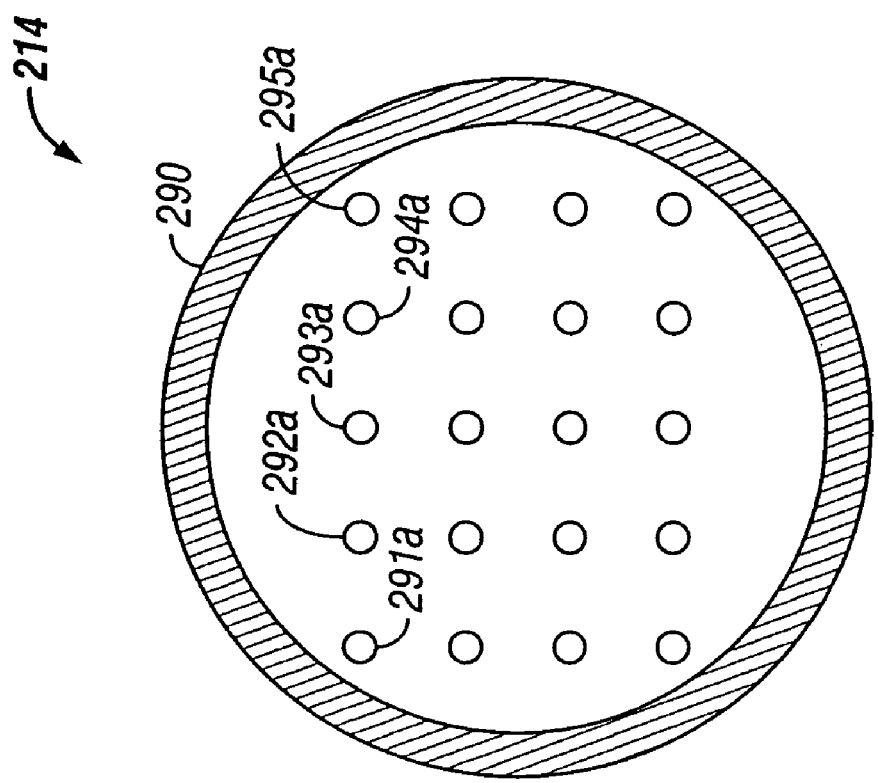
Figure 2C:
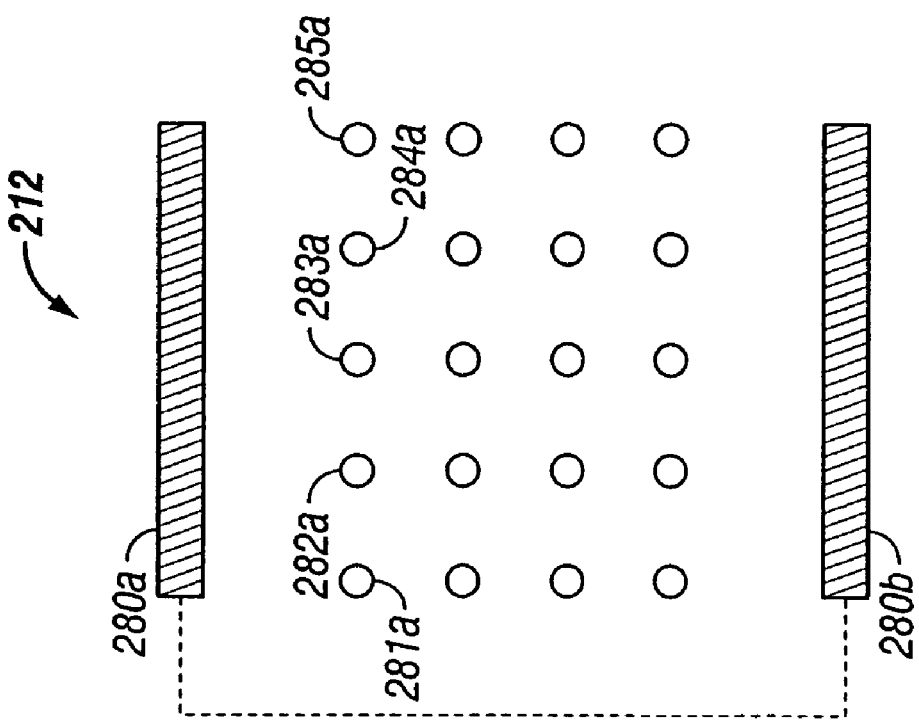

FIG. 2C is a functional diagram of an alternative configuration for an electrode set 212. The electrode set 212 includes twenty working electrodes, for example 281a-285a, arranged as four rows of five working electrodes. However, the working electrodes need not be arranged in a rectangular array, nor is there any significance to the number of working electrodes shown in the electrode set 212 of FIG. 2C. The counter electrode is configured as a counter electrode pair having an upper counter electrode 280a and a lower counter electrode 280b. The upper and lower counter electrodes 280a and 280b are electrically coupled and are typically at the same electrical potential. No reference electrode is included in the electrode set. However, other embodiments may include a reference electrode. The electrode set 212 configuration can be included in one or more sample wells. Typically, all of the electrode sets fabricated on a substrate have the same configuration. However, there may be some instances when it is desirable to have different electrode configurations in different sample wells.

FIG. 2D is another alternative configuration for an electrode set 214. The electrode set 214 includes twenty working electrodes, for example 291a-295a, arranged as four rows of five working electrodes. Again, the number of electrodes and the rectangular arrangement shown in FIG. 2D are only provided as examples and are not limitations on the electrode configuration. A counter electrode 290 is configured as a single continuous electrode encircling all of the working electrodes, for example 291a-295a. No reference electrode is included in the electrode set 214. However, other embodiments can include a reference electrode. The electrode set 214 configuration can be included in one or more sample wells.

Figure 3A:
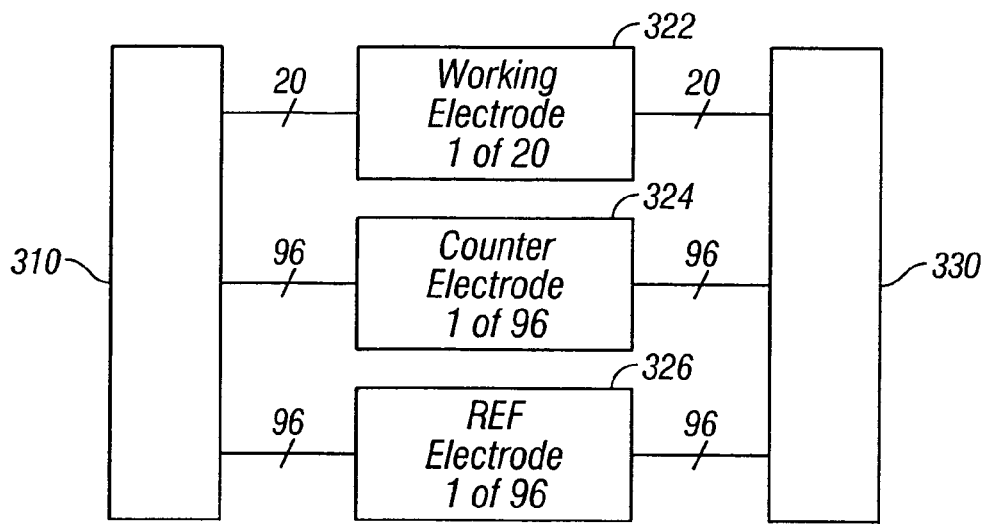
FIGS. 3A-3C are functional block diagrams of alternative electrode multiplexing configurations.
Figure 3B:
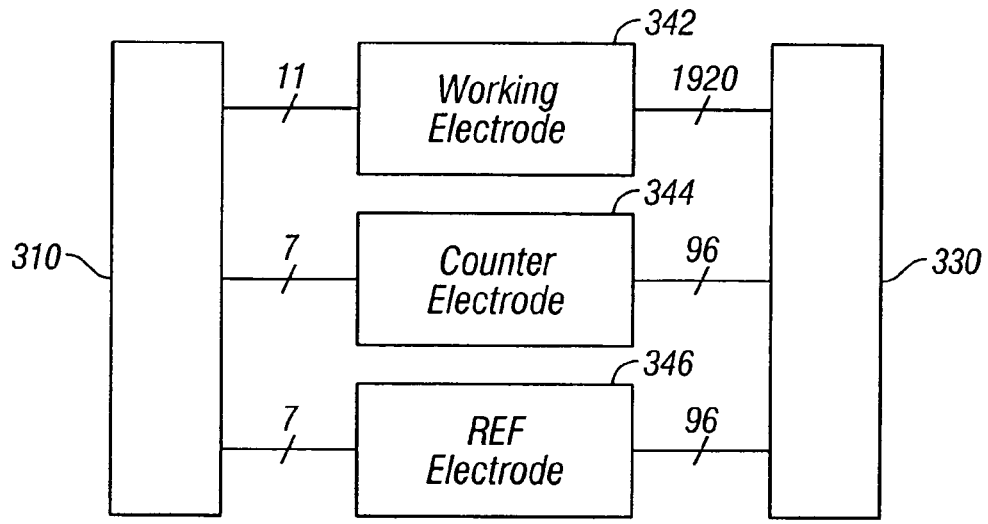
Figure 3C:
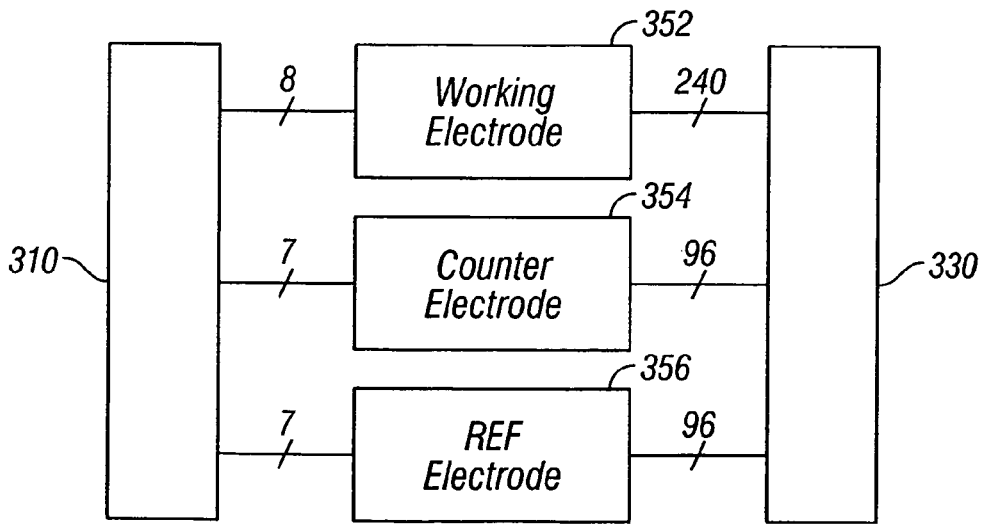

FIGS. 3A-3C are functional block diagrams of alternative multiplexing schemes that may be used to reduce the number of contact pads on the substrate while maintaining the ability to individually analyze each sample well. Each of the functional block diagrams is configured for a 96 well plate having 20 working electrodes, 1 counter electrode, and 1 reference electrode positioned in each sample well. However, similar multiplexing schemes may be used with other sample array configurations and other electrode configurations.

FIGS. 3A-3C shows functional block diagrams of modules that can be included in a sample array that is configured according to differing multiplexing schemes. FIG. 3A shows a functional block diagram of a first multiplexing scheme. In the scheme shown in FIG. 3A, each of the working electrodes in the sample wells are coupled to corresponding working electrodes in other sample wells. This configuration is discussed above in relation to FIG. 2B. Each counter electrode is individually controlled. Additionally, each reference electrode is individually controlled.

A connector interface 310, which can be an array of contact pads, is coupled to a working electrode multiplexer 322, a counter electrode multiplexer 324, and a reference electrode multiplexer 326. The multiplexers in turn are coupled to the electrode array 330. The electrode array 330 represents the entire collection of electrodes in all of the electrode sets in the sample array.

In this embodiment, the working electrode multiplexer 322, counter electrode multiplexer 324, and reference electrode multiplexer 326 can be configured as electrical connections connecting the connector interface 310 to the respective electrodes in the electrode array 330. A controller can select any one working electrode from the 20 available working electrodes. The controller can apply a potential to the selected working electrode. The corresponding working electrodes in the other sample wells will also receive the potential. The controller can energize electrodes in a particular sample well by applying a potential to the counter electrode and reference electrode of the desired sample well.

FIG. 3B shows a functional block diagram of a second multiplexing scheme. As was the case with the first multiplexing scheme, a connector interface 310 connects to working, counter, and reference multiplexers, 342, 344, and 346 respectively. The multiplexers, 342, 344, and 346 are in turn coupled to the electrodes in an electrode array 330.

In the second multiplexing scheme, each working electrode from the electrode array 330 is individually coupled to a working electrode multiplexer 342. Similarly, each counter electrode is individually coupled to a counter electrode multiplexer 344 and each reference electrode is individually coupled to a reference electrode multiplexer 346. Unlike the previous multiplexing scheme, no two electrodes are commonly connected in the second multiplexing scheme. Preferably, the multiplexers 342, 344, 346, are built into or are permanently attached to the Substrate 20.

Each of the multiplexers, 342, 344, and 346, operates as a logical decoder. For example, at least an 11-bit logical decoder is required to individually address each of the 1920 working electrodes. An 11-bit decoder can individually address 2048 lines ($2^{11}=2048$) which is greater than 1920, the number of working electrodes. Similarly at least a 7-bit decoder is required to individually address the 96 independent counter electrodes. Similarly, at least a 7-bit decoder is required to individually address the 96 independent reference electrodes.

Thus, the working electrode multiplexer 342 can include an 11-bit logical decoder to address a particular working electrode and supporting electronics that are configured to apply the desired potential to the addressed working electrode. Similarly, the counter electrode multiplexer 344 can include a 7-bit logical decoder and supporting electronics that are configured to apply a desired potential to an addressed counter electrode. The reference electrode multiplexer 346 can include a 7-bit decoder and supporting electronics that are configured to apply a desired potential to an addressed reference electrode.

Thus, using the second multiplexing scheme, only 25 connections are required on the connector interface 310. However, the design of the multiplexers, particularly the working electrode multiplexer 342, is more complicated, and the cost of the substrate 20 is increased somewhat by the incorporation of active electronics.

FIG. 3C is a functional block diagram of an embodiment of another multiplexing scheme that combines features from the multiplexing schemes shown in FIGS. 3A and 3B. In the third multiplexing scheme, each working electrode from a particular row of sample wells in the electrode array 330 is coupled to corresponding working electrodes in the row. Thus, in a 96-well plate having 12 rows of 8 sample wells, each working electrode in a row is coupled to eight other working electrodes. The common working electrodes are then coupled to a working electrode multiplexer 352. Each counter electrode is individually coupled to a counter electrode multiplexer 354 and each reference electrode is individually coupled to a reference electrode multiplexer 356.

As in the multiplexer embodiment of FIG. 3B, each of the multiplexers, 352, 354, and 356, operates as a logical decoder. The working electrode multiplexer 352 can use a 8-bit decoder, where 5 bits are used to identify the working electrode from 20 possible electrodes and 3 bits are used to identify the particular row from 12 possible rows. As in the embodiment of FIG. 3B, the counter electrode multiplexer 354 can include a 7-bit logical decoder and supporting electronics that are configured to apply a desired potential to an addressed counter electrode. The reference electrode multiplexer 356 can include a 7-bit decoder and supporting electronics that are configured to apply a desired potential to an addressed reference electrode. Thus, a total of 22 contact pads are required at the connector interface 310.

Figure 4:
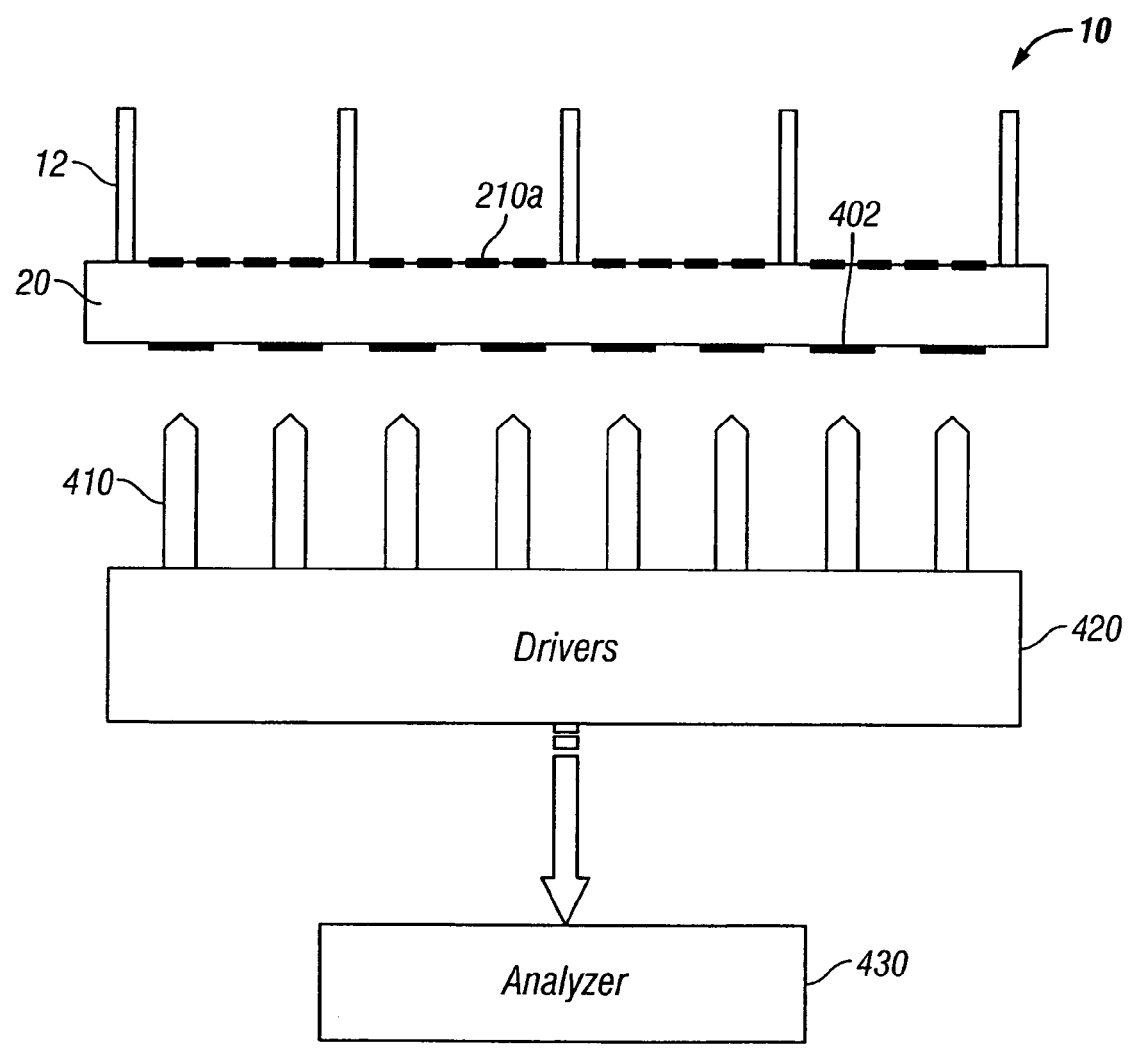
FIG. 4 is a cross sectional view of the interface of an analyzer to a portion of a sample well array.

Regardless of the multiplexing scheme used by the system, the contact pads on the sample array are coupled to an analyzer via a connector interface. FIG. 4 is a functional block diagram of an embodiment of a multiplexed sample analysis system. The functional diagram of FIG. 4 is a cross section showing a sample array 10 coupling to a connector interface of an electrochemical analysis instrument.

A sample array 10 having a well plate 12 bonded to a substrate 20, such as the sample array of FIG. 1A, can include one or more electrode sets, for example 210a, positioned in one or more of the sample wells. The electrode sets, for example 210a, can be coupled to contact pads 402 positioned, for example, in a connector interface on the side of the substrate 20 opposite the well plate 12.

The electrode sets, for example 210a, can be coupled to the contact pads 402 using a multiplexing scheme. The number of contact pads 402 in the connector interface may be greater than, equal to, or less than the number of electrodes depending on the mutliplexing scheme used.

In one embodiment, the contact pads 402 are carbon electrodes. In another embodiment, the contact pads 402 are gold electrodes. The contact pads 402 may be fabricated on the substrate or may be bonded or otherwise attached to the substrate. The contact pads 402 can be conductive pads, springs, sockets, plugs, and the like, or some other means for connection.

When analyzing the samples in the sample array 10, the sample array 10 is disposed on analysis instrumentation so as to couple the contact pads 402 to corresponding connections 410 on the analysis instrumentation. The connections 410 can be spring contacts or spring loaded probes that connect with the contact pads 402 on the sample array 10. In other embodiments, the connections 410 can be conductive pads, springs, sockets, plugs, and the like, or some other complementary means for connection.

The connections 410 are coupled to a multiplexer 420 that is in turn coupled to an analyzer 430. The multiplexer 420 can be used to apply a potential to the electrodes, e.g. 210a, of the sample array 10. Additionally, the multiplexer 420 can be used to couple signals from the electrodes, e.g. 210a, to the analyzer 430 for analysis.

In one embodiment, the analyzer 430 controls the multiplexer 420 to apply a potential across a particular working electrode and counter electrode pair on the sample array 10. Then, the analyzer 430 performs, for example, coulometry or amperometry to determine if the sample in the sample well hybridized with a polymer probe captured on the working electrode.

Figure 5:
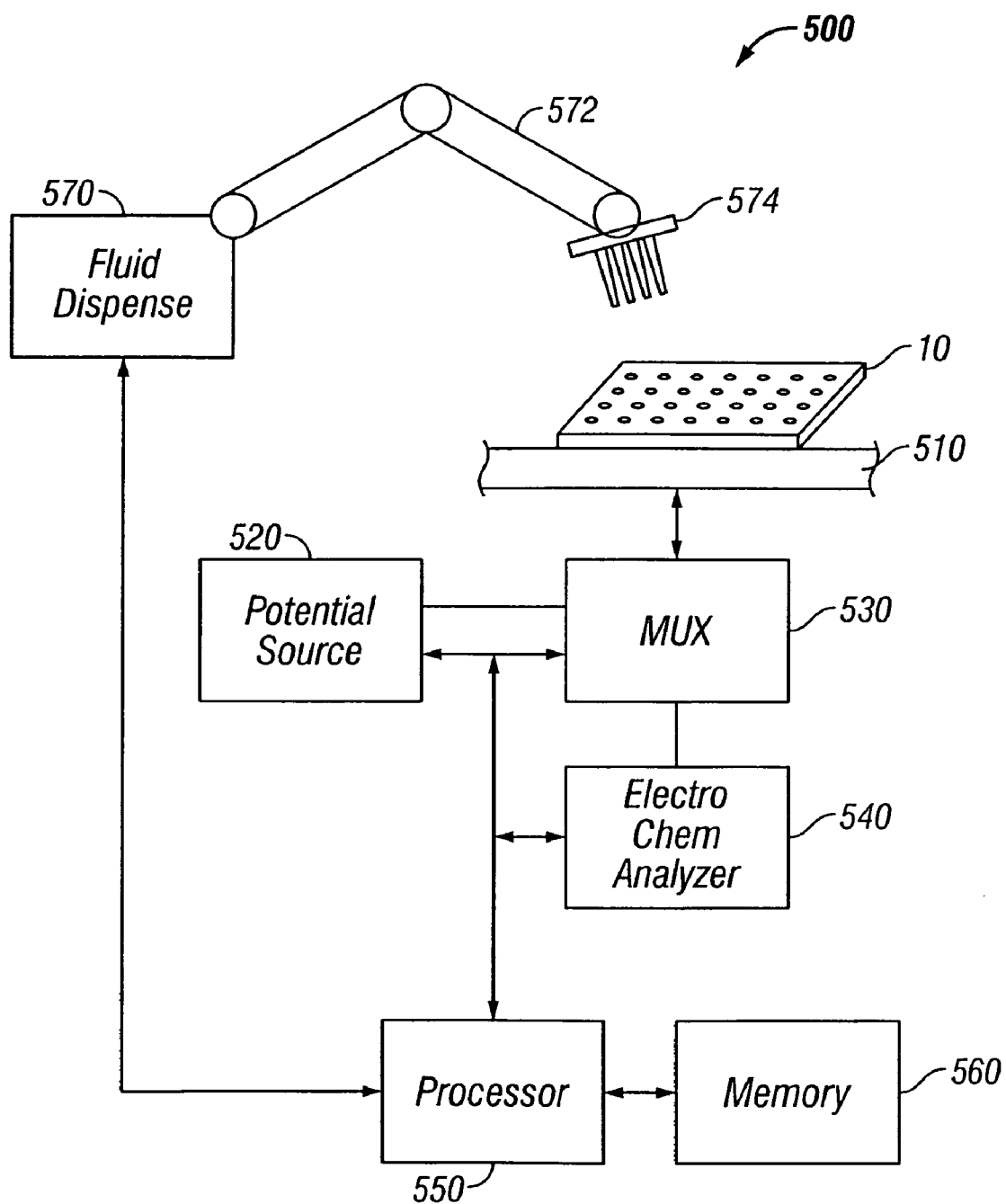
FIG. 5 is a functional block diagram of a multiplexed sample detection system.

FIG. 5 is a functional block diagram of a sample analysis system 500 configured to detect hybridization of samples to captured probes contained within a sample array 10. The sample array 10 can, for example, be the sample array 10 of FIG. 1A having the multiplexing scheme shown in FIG. 2B. The sample array 10 can be positioned on a receiving platform 510 of a sample analysis system 500. The receiving platform 510 can include a connection interface that has spring probes that couple to the contact pads on the bottom of the sample array 10. The spring probes may be advantageous due to the long life cycle associated with such a connection. A spring probe can have, for example, a life cycle in excess of millions of cycles.

The spring probes can couple signals to and from the sample array 10. The spring probes in the receiving platform 510 are coupled to a multiplexer 530. The multiplexer 530 can be configured to decode signals to and from the sample array 10 in accordance with the multiplexing scheme implemented on the sample array 10.

A potential source 520 is coupled to the multiplexer 530. The potential source can be controlled to apply a potential to a desired working electrode, counter electrode, and optionally, a reference electrode.

An electrochemical analyzer 540 is coupled to the multiplexer 530 and can be configured to electrochemically detect hybridization of samples in the sample well having energized electrodes. A processor 550 in communication with memory 560 can be coupled to the potential source 520, multiplexer 530, and electrochemical analyzer 540 to control the operation of a hybridization detection process.

For example, the processor 550 can operate according to processor readable instructions stored in the memory 560 to control the operation of the potential source 520, multiplexer 530, and electrochemical analyzer 540. The processor 520, in response to processor readable instructions, can instruct the multiplexer to select a particular working electrode and counter electrode pair corresponding to a particular sample well. The processor 550 can then control the potential source to apply a potential to the selected working electrode and sample electrode.

The processor 540 can then instruct the electrochemical analyzer 540 to perform detection on the selected sample well. The electrochemical analyzer can, for example detect hybridization to a captured polymer probe based in part on coulometry or amperometry. The processor 550 can also read the results from the electrochemical analyzer and store the results in memory 560 for subsequent access. The processor can then instruct the multiplexer 530 to select another pair of electrodes in the same or different sample well and repeat the analysis until all desired sample wells and probe pairs have been tested.

To further automate the process, an automated fluid handling system may be integrated with the sample analysis system 500. The fluid handling system can include a fluid dispenser 570 coupled to a robotic arm 572 that is configured to deliver fluid to one or more pipettes 574. The processor 550 can be configured to control the fluid dispenser 570 and robotic arm 572 to dispense reagent into one or more sample wells in the sample array 10. It may be advantageous to configure the sample array 10 to have the dimensions of a standard well plate, such as a 96-well plate in order to allow the system 500 to utilize existing automated fluid handling systems.

Figure 6:
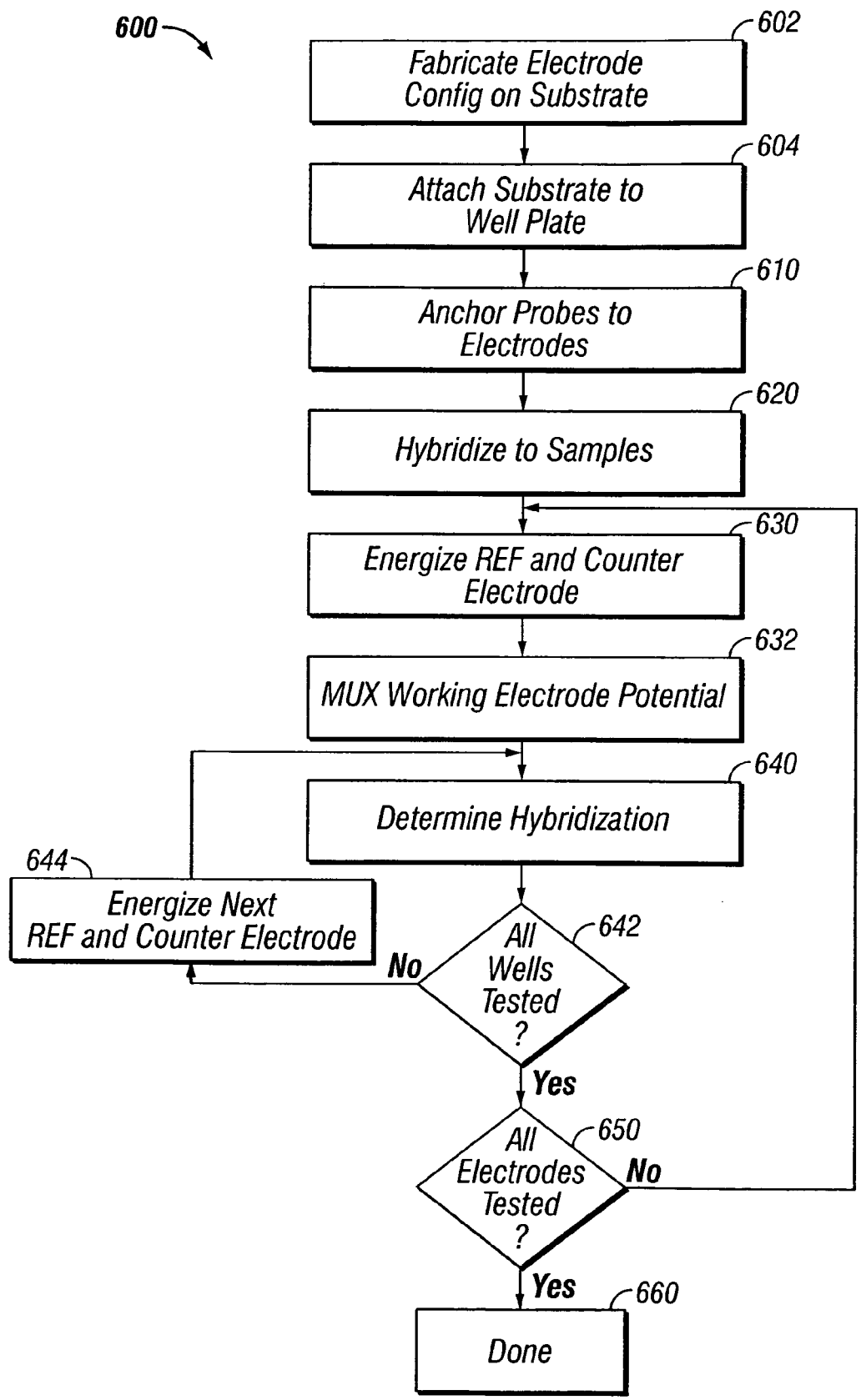
FIG. 6 is a flowchart of a method of multiplexed sample detection.

FIG. 6 is a flowchart of a method of analyzing samples for hybridization to captured probes in a multiplexed sample array. The discussion provided above, of sample arrays, electrode configurations, multiplexing, and electrochemical detection, demonstrates that the order of process in the method 600 may be altered without deviating from the desired result. Additionally, one or more steps may be modified, omitted from the method 600, or added to the method 600 while not substantially affecting the method.

The method 600 begins at block 602 by fabricating an electrode configuration on a substrate. A typical printed circuit board manufacturing process can be used to fabricate the substrate. This process can also include fabricating the electrical connections and placement of the devices required to implement the multiplexing scheme onto the substrate. After fabricating the electrode configuration, the substrate is bonded to a bottomless well plate in step 604. This step may be performed by automated machinery configured to handle the well plate, substrate, and bonding adhesive.

Once the substrate is bonded to the well plate, the assembled well plate is forwarded to a system that anchors probes to the working electrodes in the sample wells. An automated process for capturing single stranded probes onto the working electrodes may be used. Alternatively, the probes can be attached to working electrodes prior to binding the substrate to the well. Once the sample arrays are prepared with captured probes, sample analysis can proceed using a sample analysis system such as the system shown in FIG. 5.

At block 620 samples are introduced to the sample wells and may hybridize to the captured probes. As shown in FIG. 5, the sample analysis system can include a fluid handling system that introduces reagents to the sample array. Hybridization of target strands to the captured probes may occur in some of the sample wells.

After hybridizing the samples, the sample analysis system proceeds to block 630 where a first counter electrode and reference electrode are energized. Energizing refers to the application of a potential to the electrode. As noted above, the inclusion of a reference electrode is optional and may be omitted in some embodiments.

After applying the potential to the first reference and counter electrodes, the sample analysis system proceeds to block 632 and applies a potential to a first working electrode. The sample analysis system can apply the potential to the working electrode using the multiplexing scheme implemented on the sample array.

The sample analysis system next proceeds to block 640 where the system determines if any targets in the sample have hybridized with the captured probes on the working electrode. The sample analysis system can, for example, determine hybridization using electrochemical detection.

The sample analysis system next proceeds to decision block 642 to determine if all sample wells have been tested. In the multiplexing scheme discussed in association with FIG. 2B, all corresponding working electrodes are connected in common. Thus, it may be advantageous to first measure hybridization to the corresponding electrode in all sample wells before applying a potential to another working electrode.

If not all sample wells have been tested, the sample analysis system proceeds from decision block 642 to block 644 where the potential is removed from the current counter electrode and reference electrode and a potential is applied to the next counter and reference electrodes. The sample analysis system then proceeds back to block 640.

Returning to decision block 642, if all sample wells have been tested, the sample analysis system proceeds to decision block 650 to determine if all working electrodes have been tested. If not, the sample analysis system proceeds back to block 630 where the initial counter and reference electrodes are energized and then proceeds to block 632 where the next working electrodes are energized.

If, at decision block 650 all of the electrodes have been tested, the sample analysis system has tested all electrode combinations in all of the sample wells. The sample analysis system proceeds to block 660 and is done testing the sample array.

In this manner, inexpensive, flexible sequence analysis can be performed using a sample array having electrode sets positioned in a plurality of sample wells. The electrode sets can include carbon electrodes having captured polymer probes. The sample array can implement a multiplexing scheme to reduce the number of connections that need to be made to an associated analyzer. The analyzer can selectively apply potentials to the electrodes and electrochemically detect probe hybridization using electrochemical techniques.

It should be noted that the steps of the method represented in FIG. 6 are relatively flexible, and the method may not necessarily include all of the steps mentioned. For example, in some embodiments, the steps of manufacturing and preparing the well plate (e.g., blocks 602 and perhaps 604 and/or 610 and 620) may be done by a first party, and constitute a first method of the present invention. Then, some or all of the remaining steps (blocks 620 or 630 to block 660) may be performed as a second method of the present invention by a different party.

For example, in block 632, the act of energizing reference and counter electrodes can refer to energizing all working electrodes in a sample well and the corresponding one or more counter electrodes in that sample well. In block 640, the act of determining hybridization then refers to determining whether targets have hybridized to captured probes on each of the working electrodes. For example, an electrochemical detection technique may be performed on each working electrode individually or on multiple electrodes simultaneously.

The method 600 then proceeds to blocks 642 and 644 as described above. However, decision block 650 could be eliminated from the method 600 because all working electrodes within a sample well can be simultaneously energized and tested.

In still other embodiments of the method 600, the act of energizing working electrodes of block 632 may refer to applying a potential to a number of working electrodes that is less than all of the working electrodes within a sample well. Then, decision block 650 would still be included, and subsequent acts of energizing working electrodes would refer to energizing one or more working electrodes not previously energized.

When the multiplexing technique of FIG. 2B is combined with the modified method 600, the number of times electrodes are energized can be minimized. Applying an electrical potential to all working electrodes within a selected sample well also results in the application of the potential to working electrodes in all other sample wells. Then, the sample analysis system need only sequentially control the potential applied to the various counter electrodes.

In one embodiment, the substrate 20 with all electrodes and electrical connections and the well plate 12 are manufactured as separate items, and sold as a kit, optionally together with a means for fastening the two together (e.g., the adhesive layer 14, which may be a separate sheet or may be pre-applied to either the well plate 12 or the substrate 20, preferably with a protective release sheet (not shown)). This would allow an end user to more conveniently attach desired probes to the working electrodes because those electrodes are more easily accessible prior to attachment of the well plate 12. Thus, a method of the present invention could comprise attaching the probes to the substrate 20, then assembling the substrate 20 to the well plate 12, optionally then followed by analytical steps (e.g., contacting the electrodes with sample by adding sample to wells, addressing the electrodes in turn, and taking a measurement to ascertain the presence or absence of a desired analyte in one or more of the wells).

Electrical connections, couplings, and connections have been described with respect to various devices or elements. The connections and couplings may be direct or indirect. A connection between a first and second device may be a direct connection or may be an indirect connection. An indirect connection may include interposed elements that may process the signals from the first device to the second device.

Those of skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons may implement the described functionality in varying ways for each particular application, but such implementation decisions should not be interpreted as causing a departure from the scope of the invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. A storage medium can be coupled to the processor such the processor can read information from, and write information to, the storage medium. In the alternative, the storage medium may be integral to the processor. The processor and the storage medium may reside in an ASIC.

The above description of the disclosed embodiments is provided to enable any person skilled in the art to make or use the invention. Various modifications to these embodiments will be readily apparent to those skilled in the art, and the generic principles defined herein may be applied to other embodiments without departing from the spirit or scope of the invention. Thus, the invention is not intended to be limited to the embodiments shown herein but is to be accorded the widest scope consistent with the principles and novel features disclosed herein.

What is claimed is:

1. An electrochemical detection system comprising:
a connection interface configured to electrically connect with contact pads of a sample array, the sample array comprising a plurality of zones each comprising a plurality of working electrodes, wherein at least one polymer probe is attached to each of the working electrodes and each zone is associated with a single counter electrode;
a multiplexer coupled to the connection interface and configured to selectively apply an electric potential to one of the plurality of electrodes in each of the zones by applying the electric potential to a single electrical connection in the connection interface, wherein the single electrical connection in the connection interface couples an electrode in each of the zones to the electric potential, the multiplexer being further configured to selectively apply an opposing electric potential to a selected counter electrode positioned proximate a selected zone in the sample array via the connection interface so that a current flows between only the one of the plurality of electrodes in the selected zone and the counter electrode; and
an analyzer configured to electrochemically detect at least one property of a sample in the selected zone based in part on the current.

2. The system of claim 1, wherein a second connection on the connection interface is electrically coupled to the counter electrode in the sample array.

3. The system of claim 1, wherein the analyzer is configured to detect hybridization of the sample.

4. The system of claim 1, wherein the analyzer is configured to detect the property based on coulometry.

5. The system of claim 1, wherein the analyzer is configured to detect the property based on amperometry.

6. The system of claim 1, further comprising a fluid dispenser configured to deliver a reagent to at least one well in the sample array.

7. A sample array for an electrochemical detection system, the sample array comprising:
a first sample well;
a second sample well;
a substrate bonded to the first and second sample wells;
a first electrode set comprising a plurality of working electrodes each coupled to at least one polymer probe, the first electrode set being positioned on the substrate in the first sample well; and
a second electrode set comprising a plurality of working electrodes each coupled to at least one polymer probe, the second electrode set being positioned in the second sample well, wherein at least one of the plurality of working electrodes positioned in the second sample well is electrically coupled to a corresponding working electrode in the first sample well via only an electrical connection of the sample array.

8. The sample array of claim 7, further comprising a plurality of polymer probes coupled to the working electrodes in the first electrode set.

9. A sample array for an electrochemical detection system, the sample array comprising:
a plurality of sample wells;
a substrate bonded to the plurality of sample wells;
a plurality of working electrodes positioned on a first side of the substrate, with at least two working electrodes positioned in each of the plurality of sample wells; and
at least one multiplexer selectively coupling contact pads positioned on the substrate to the plurality of working electrodes, wherein a single contact pad of the substrate is coupled to a single working electrode of each sample well such that an electric potential applied to a particular contact pad will be applied to a single working electrode in each sample well, and wherein the sample array comprises a single structure configured for coupling with a sample analyzer.

10. The sample array of claim 9, further comprising a plurality of counter electrodes positioned on the first side of the substrate, with at least one counter electrode positioned in each of the plurality of sample wells.

11. A method of detecting hybridization, the method comprising:
introducing a sample to a plurality of sample wells, each sample well comprising (1) a plurality of probes each coupled to one of a plurality of working electrodes and (2) a counter electrode;
applying a first potential to a first contact pad that is electrically coupled to a single working electrode in each of at least two different sample wells;
applying a second potential to a second contact pad that is electrically coupled to only one counter electrode; and
electrochemically detecting hybridization of the sample to at least one of the plurality of probes.

12. A sample array comprising:
at least a first well and a second well;
a substrate bonded to each of the first and second wells;
a plurality of working electrodes positioned on the substrate such that at least two working electrodes are positioned in each of the wells, wherein each working electrode in the first well is electrically coupled with a corresponding working electrode in the second well; and
at least one multiplexer selectively coupling a first electrical potential to at least one corresponding working electrode in each of the first and second wells via a single electrical lead from the multiplexer, the at least one multiplexer further coupling a second electrical potential to a counter electrode associated with each of the working electrodes of the first well.

13. The sample array of claim 12, further comprising a third well comprising at least two working electrodes positioned in the third well, wherein each of the working electrodes in the first well is electrically c6upled with a corresponding working electrode in the second well and a corresponding working electrode in the third well.

14. The sample array of claim 12, wherein the first electrical potential is coupled to each of the plurality of working electrodes.

15. The sample array of claim 12, wherein the first electrical potential is coupled to only one corresponding working electrode in each of the first and second wells.

16. A method of electrochemical analysis comprising:
depositing at least one sample into a plurality of sample wells, each sample well comprising (1) a counter electrode, and (2) a plurality of probes each coupled to at least one of a plurality of working electrodes;
applying a first potential to each of the plurality of working electrodes in each of the plurality of sample wells;
applying a second potential to a first counter electrode associated with a first of the plurality of sample wells; and
electrochemically detecting hybridization of the sample in the first well to at least one of the plurality of probes.

17. The method of claim 16, wherein each working electrode in a first of the plurality of wells is electrically coupled to a corresponding working electrode in each of the remaining plurality of wells.

18. The method of claim 16, further comprising:
electrically isolating the second potential from the first counter electrode;
applying the second potential to a second counter electrode associated with a second of the plurality of sample wells; and
electrochemically detecting hybridization of the sample in the second well to at least one of the plurality of probes.

19. The method of claim 18, further comprising:
electrically isolating the second potential from the second counter electrode;
applying the second potential to a third counter electrode associated with a third of the plurality of sample wells; and
electrochemically detecting hybridization of the sample in the third well to at least one of the plurality of probes.

* * * * *

UNITED STATES PATENT AND TRADEMARK OFFICE
CERTIFICATE OF CORRECTION

PATENT NO. : 7,341,834 B2 Page 1 of 1
APPLICATION NO. : 11/011490
DATED : March 11, 2008
INVENTOR(S) : Xing Yang It is certified that error appears in the above-identified patent and that said Letters Patent is hereby corrected as shown below:

At Column 16, Line 17, please delete "c6upled" and insert therefore, -- coupled --.

Signed and Sealed this

Thirtieth Day of September, 2008

JON W. DUDAS
*Director of the United States Patent and Trademark Office*